(12) United States Patent
Carlson et al.

(10) Patent No.: US 12,421,456 B2
(45) Date of Patent: Sep. 23, 2025

(54) PROCESS FOR CHEMICALLY RECYCLING PLASTIC WASTE WITH ALKANE OXIDATION PRODUCTS

(71) Applicant: Anellotech, Inc., Pearl River, NY (US)

(72) Inventors: Torren Carlson, Pearl River, NY (US); Leslaw Mleczko, Dormagen (DE); Omar M. Basha, Wilmington, DE (US)

(73) Assignee: Anellotech, Inc., Pearl River, NY (US)

( * ) Notice: Subject to any disclaimer, the term of this patent is extended or adjusted under 35 U.S.C. 154(b) by 45 days.

(21) Appl. No.: 17/964,025

(22) Filed: Oct. 11, 2022

(65) Prior Publication Data

US 2024/0117254 A1 Apr. 11, 2024
US 2025/0197731 A9 Jun. 19, 2025

(51) Int. Cl.
*C10G 1/10* (2006.01)
*C07C 1/22* (2006.01)
*C07C 5/48* (2006.01)
*C10G 1/00* (2006.01)

(52) U.S. Cl.
CPC .......... *C10G 1/10* (2013.01); *C07C 1/22* (2013.01); *C07C 5/48* (2013.01); *C10G 1/002* (2013.01); *C10G 2300/1003* (2013.01); *C10G 2400/20* (2013.01); *C10G 2400/30* (2013.01)

(58) Field of Classification Search
None
See application file for complete search history.

(56) References Cited

U.S. PATENT DOCUMENTS

| | | |
|---|---|---|
| 4,029,716 A | 6/1977 | Kaeding |
| 4,567,307 A | 1/1986 | Jones et al. |
| 5,012,028 A | 4/1991 | Gupta et al. |
| 5,336,825 A | 8/1994 | Choudhary et al. |
| 6,596,912 B1 | 7/2003 | Lunsford et al. |
| 7,183,451 B2 | 2/2007 | Gattis et al. |
| 7,667,085 B2 | 2/2010 | Gattis et al. |
| 8,710,286 B2 | 4/2014 | Butler |
| 10,793,490 B2 | 10/2020 | Radaelli et al. |
| 11,046,625 B1 * | 6/2021 | Sofranko .............. C07C 5/48 |
| 11,046,892 B1 * | 6/2021 | Sofranko .............. C07C 4/025 |
| 11,542,214 B2 | 1/2023 | Radaelli et al. |
| 2020/0362248 A1 | 11/2020 | Cartolano et al. |
| 2024/0059629 A1 | 2/2024 | Goyheneix et al. |

OTHER PUBLICATIONS

Kato K., and C. Y. Wen. "Bubble assemblage model for fluidized bed catalytic reactors." Chemical Engineering Science 24.8 (1969): 1351-1369.

Bhatia S., et al, "Oxidative coupling of methane (OCM) in a catalytic membrane reactor and comparison of its performance with other catalytic reactors," Chem Eng. J., 148 (2-3), 2009, 525-53.

(Continued)

*Primary Examiner* — Tam M Nguyen
(74) *Attorney, Agent, or Firm* — Frank Rosenberg

(57) ABSTRACT

A method of producing olefinic and aromatic hydrocarbons from waste plastics comprising feeding a mixture of plastics along with the products of the oxidation of light hydrocarbons to a process in which the feed mixture is catalytically pyrolyzed to produce olefins and aromatics.

22 Claims, 6 Drawing Sheets

(56) References Cited

OTHER PUBLICATIONS

Huber G.W. et al, "Synthesis of Transportation Fuels from Biomass: Chemistry, Catalysts, and Engineering," Chem. Rev. 106, (2006), pp. 4044-4098.

Mleczko L., Gayko, G., Niemi, V. M., & Hiltunen, J. "Reaction engineering studies in a polytropic fixed-bed reactor over a highly active and selective catalyst for oxidative methane coupling", Chemical Engineering & Technology: Industrial Chemistry-Plant Equipment-Process Engineering-Biotechnology, 20(1) (1997) 29-35.

Zavyalova Ulyana, et al. "Statistical analysis of past catalytic data on oxidative methane coupling for new insights into the composition of high-performance catalysts." ChemCatChem 3.12 (2011): 1935-1947.

Written Opinion of the International Search Authority from International Application No. PCT/US2023/076586 dated Jan. 23, 2024.

International Search Report from International Application No. PCT/US2023/076586 dated Jan. 23, 2024.

* cited by examiner

PROCESS FOR CHEMICALLY RECYCLING PLASTIC WASTE WITH ALKANE OXIDATION PRODUCTS

FIELD OF THE INVENTION

This disclosure relates to the conversion of waste plastics, polymers, and other waste materials to useful chemical and fuel products such as paraffins, olefins, and aromatics comprising feeding a mixture of plastics along with the products of the oxidation of light hydrocarbons to a process in which the feed mixture is catalytically pyrolyzed anaerobically to produce olefins and aromatics.

INTRODUCTION

Of the estimated 44 million metric tons of plastic waste managed in 2019 in the USA, approximately 86% was landfilled, 9% was combusted, and 5% was recycled, according to a 2022 study by NREL (Milbrandt et al, "Quantification and evaluation of plastic waste in the United States," Resources, Conservation & Recycling, 183, August 2022). World-wide over 368 million tons of plastics were produced. By some estimates, of the 8.3 billion tons of plastics ever produced, 6.3 billion tons ended up as waste, of which only 9% has been recycled. Plastic recycling recovers scrap or waste plastic and reprocesses the material into useful products. However, since China banned the import of waste plastics in 2018 the recycle rate in the US is estimated to have dropped to only 4.4%.

Plastic recycling is challenging due to the chemical nature of the long chain organic polymers and low economic returns. In addition, waste plastic materials often need sorting into the various plastic resin types, e.g. low density polyethylene (LDPE), high density polyethylene (HDPE), polypropylene (PP), polystyrene (PS), polyvinyl chloride (PVC), and polyethylene-terephthalate (PET) for separate recycling treatments. Pyrolytic and catalytic pyrolytic processes are known in which waste plastics are heated to produce products such as liquid oils, gases, and carbon black.

Plas-TCat™ is a catalytic fluid bed process using zeolite catalysts to convert polymer/plastic material, especially waste plastics that otherwise might be sent to a landfill or incinerator, to a mixed product of permanent gases, C2-C4 light olefins, C1-C4 light paraffins, and C5+ hydrocarbons including benzene, toluene, and xylenes ("BTX"), aromatic and non-aromatic naphtha range molecules, C11+ hydrocarbons, coke and char, and minor byproducts. Plastic mixtures that have relatively high hydrogen to carbon molar ratio, such as polyethylene (PE), polypropylene, polystyrene, and combinations thereof, can be converted to olefins and aromatics.

Chemical plastics recycling plants are limited in capacity due to the limited amount of available waste plastics in any one location; plastic waste generation is widely distributed. This resource limitation puts them at an economic disadvantage compared to petroleum-based processes that benefit from the economies of scale that are available with massive facilities. The present disclosure describes an integrated process that includes an alkane oxidation step to provide additional olefins and thermal energy to the catalytic pyrolysis of plastics to increase the yield of BTX, olefins, or both. The combined process permits closer integration of plastics recycling with conventional hydrocarbon upgrading facilities, i.e. refineries, that benefits both the plastics recycling and the refinery by introducing an avenue for monetizing methane or a light hydrocarbon mixture beyond its value as a fuel.

Numerous patents have described processes for reaction of methane or other hydrocarbons with oxygen to form olefins. For example, Jones et al in U.S. Pat. No. 4,567,307 disclose a process for upgrading methane by contacting methane with a reducible metal oxide to form ethylene that is then oligomerized catalytically to form higher hydrocarbons. Gupta et al in U.S. Pat. No. 5,012,028 describe a process for producing higher hydrocarbons by first oxidizing methane and then pyrolyzing the oxidation products in the presence of higher hydrocarbons separated from natural gas. U.S. Pat. No. 5,336,825 to Choudhary discloses a process for oxidizing methane to a mixture containing ethylene and upgrading the ethylene mixture to higher hydrocarbons over a zeolite catalyst. In U.S. Pat. No. 6,596,912 Lunsford et al disclose catalytically reacting methane and O2 at 800° C. to convert the methane to ethylene, and catalytically oligomerizing the ethylene product to C4+ products over H-ZSM-5 zeolite catalyst. Gattis et al in U.S. Pat. Nos. 7,183,451 and 7,667,085 similarly describe a process for converting natural gas to higher hydrocarbons by the oxidation of natural gas and conversion of the olefins to higher hydrocarbons over a catalyst. Butler in U.S. Pat. No. 8,710,286 disclose reacting methane with oxygen to form ethane, processing the ethane to ethylene, and using the heat energy produced within the facility. Radaelli et al in U.S. Pat. No. 10,793,490 disclose numerous processes for using methane oxidative coupling with processes for upgrading the ethylene produced to higher hydrocarbons. In US Nyce et al describe many processes for utilizing methane using an oxidative coupling of methane to produce ethylene, followed by conversion of ethylene to selectable higher hydrocarbon products. None of these disclosures describing methane upgrading include converting plastics to valuable chemicals.

Despite these and other efforts, there remains a need for increasing the capacity and yield of plastics chemical recycling processes and a need exists for monetizing methane and other light hydrocarbons beyond their value as fuels. The present disclosure shows how the integration of C1-C4 hydrocarbon oxidation to olefins with chemical plastics recycling produces a process that achieves higher mass yields of valuable materials like olefins and aromatics than plastics pyrolysis in isolation.

SUMMARY

In this invention, a mixture comprising polymers is converted along with products of alkane oxidation in a fluid bed catalytic pyrolysis process to produce olefins and aromatics. In one aspect, the invention provides a method of producing olefinic and aromatic hydrocarbons from waste plastics comprising feeding a stream comprising plastics to a catalytic pyrolysis reactor, reacting a stream comprising methane or ethane or alkanes having from 1 to 4 carbon atoms with oxygen to produce a product stream comprising ethylene, passing at least a portion of the product stream from the alkane oxidation to the catalytic pyrolysis reactor, reacting the mixed plastics and the alkane oxidation product stream in the catalytic pyrolysis reactor at a temperature above 350° C. to produce a vapor product, and recovering olefins, or aromatics, or some combination thereof from the vapor product.

In another aspect, the invention provides a method of converting plastics to olefins, or aromatics, or a mixture of olefins and aromatics, comprising: feeding a stream comprising plastics to a catalytic pyrolysis reactor; reacting a stream comprising methane or ethane or a mixture of C1-C4 alkanes with oxygen to produce a product stream comprising ethylene; pyrolyzing the plastics and at least a portion of the alkane oxidation products in the catalytic pyrolysis reactor at a temperature above 350° C. to form a vapor product; and recovering olefins, or aromatics, or some combination thereof from the vapor product.

Any of the inventive aspects may be further characterized by one or any combination of the following features:
- feeding a feed mixture comprising plastics to a catalytic pyrolysis reactor;
- wherein the feed mixture comprises plastics chosen from among polyethylene (PE), polypropylene (PP), polystyrene (PS), polyesters, polyethylene terephthalate (PET), polyvinyl chloride (PVC), polyvinyl dichloride (PVDC), acrylonitrile-butadiene-styrene (ABS) copolymers, polyamide, polyurethane, polyethers, polycarbonates, poly(oxides), poly(sulfides), polyarylates, polyether ketones, polyetherimides, polysulfones, polyurethanes, polyvinyl alcohols, and polymers produced by polymerization of monomers, dienes, olefins, styrenes, acrylates, acrylonitrile, methacrylates, methacrylonitrile, diacids and diols, lactones, diacids and diamines, lactams, vinyl esters, or block copolymers thereof, or alloys thereof; thermoset polymers, epoxy resins; phenolic resins; melamine resins; alkyd resins; vinyl ester resins; unsaturated polyester resins; cross-linked polyurethanes; polyisocyanurates; crosslinked elastomers, including but not limited to, polyisoprene, polybutadiene, styrene-butadiene, styrene-isoprene, ethylene-propylene-diene monomer polymer; and mixtures thereof;
- wherein the feedstock comprises a mix of waste plastic chosen from among polyethylene terephthalate (PET), high density polyethylene (HDPE), polyvinyl chloride (PVC) or polyvinylidene (PVCD), low density polyethylene (LDPE), polypropylene (PP), polystyrene (PS), or mixed resins, or some combination thereof;
- wherein the feed mixture of plastics comprises waste plastics;
- wherein the feed mixture of plastics comprises copolymers such as: ethylene-propylene, EPDM, acrylonitrile-butadiene-styrene (ABS), nitrile rubber, natural and synthetic rubber, tires, styrene-butadiene, styrene-acrylonitrile, styrene-isoprene, styrene-maleic anhydride, ethylene-vinyl acetate, nylon 12/6/66, filled polymers, polymer composites, polymer composites comprising natural fibers, plastic alloys, other polymeric materials, and polymers or plastics dissolved in a solvent, or combinations thereof;
- wherein the feed materials can comprise materials obtained from polymer or plastic manufacturing processes as waste or discarded materials, post-consumer recycled polymer materials, materials separated from waste streams such as municipal solid waste (MSW), black liquor, wood waste, or other biologically produced materials, or combinations thereof;
- wherein a stream comprising methane or ethane or a mixture of $C_1$-$C_4$ alkanes is reacted with oxygen to produce a product stream comprising ethylene;
- wherein the feed mixture to the oxidation reactor comprises no more than 5, or 10, or 25, or 50, or 85% by volume of any one of $CO_2$, CO, $N_2$, He, or $H_2O$ or any combination thereof;
- wherein at least a portion of the products from alkane oxidation is passed to the catalytic pyrolysis reactor;
- wherein heat is recovered from the product stream from the alkane oxidation before a portion of it is fed to the catalytic pyrolysis reactor;
- wherein the alkane oxidation is conducted in the presence of a catalyst;
- wherein the oxidation reactor comprises a fixed bed or fluid bed reactor;
- wherein the maximum temperature in the oxidation reactor is at least 500, or 600, or 700, or 800, or 850° C., or no more than 1000, or 950, or 900, or 850° C., or from 500 to 950, or from 600 to 900, or from 700 to 850° C.;
- wherein the residence time of the alkane in the oxidation reactor is no more than 2, or 1, or 0.5, or 0.3, or 0.2, or from 0.01 to 2, or from 0.05 to 1, or from 0.2 to 0.5 seconds;
- wherein the weight hourly space velocity of the feed gas to the oxidation reactor is at least 3,000, or 5,000, or 8,000, or 10,000, or 15,000 $cm^3$/g-cat-hr, or from 3,000 to 25,000, or from 5,000 to 15,000, or from 8,000 to 12,000 $cm^3$/g-cat-hr.
- wherein the feed to the oxidation reactor has a ratio of oxygen to carbon atoms of no more than 1.0, or 0.9, or 0.8, or 0.7, or 0.5, or 0.3, or from 0.2 to 1.0, or from 0.25 to 0.9, or from 0.3 to 0.7;
- wherein at least a portion of the feed to the oxidation reactor comprises natural gas or biogas or methane derived therefrom;
- wherein the catalytic pyrolysis reactor is a fluidized bed reactor;
- wherein the plastics and at least a portion of the product from the alkane oxidation react in the presence of a catalyst in a fluidized bed catalytic reactor to form a product vapor mixture;
- wherein the non-vapor products of the catalytic pyrolysis, or a portion of the gases remaining after removal of desired products, or both, are combusted to provide energy for the catalytic pyrolysis process;
- wherein a portion of the heat generated from the alkane oxidation may be used to heat the pyrolysis reactor or to heat the fluidization gas to the regenerator, or as a heat source for other elements of the process;
- wherein the catalytic pyrolysis reaction is conducted in a fluidized bed, circulating bed, bubbling bed, or riser reactor at an operating temperature in the range from 300° C. to 800° C., or from 350° C. to 750° C., or from 400° C. to 700° C., or from 450° C. to 650° C., or from 500° C. to 600° C.;
- wherein the absolute pressure in the catalytic pyrolysis reactor is at least 0.1 MPa (1 bara), or at least 0.3 MPa (3 bara), or at least 0.4 MPa (4 bara), or from 0.1 to 2.0 MPa (1 to 20 bara), or from 0.1 to 1.0 MPa (1 to 10 bara), or from 0.3 to 0.8 MPa (3 to 8 bara), preferably from 0.4 to 0.6 MPa (4 to 6 bara);
- wherein the residence time of the vapors in the catalytic pyrolysis reactor can be from 0.5 second to 480 seconds, or from 0.5 second to 240 seconds, or from 2 seconds to 60 seconds, or from 3 seconds to 30 seconds, or from 4 seconds to 15 seconds;
- wherein the catalyst is a solid catalyst and the step of catalytically pyrolyzing comprises pyrolyzing in the presence of the solid catalyst in a fluidized bed reactor to produce a fluid product stream and used catalyst with coke;

wherein the catalyst comprises a zeolite;
wherein the zeolite is at least partially in its protonated form with H+ ions replacing at least some of the cations;
wherein the catalyst may be selected from naturally occurring zeolites, synthetic zeolites, and combinations thereof;
wherein the catalyst may be selected from ZSM-5, ZSM-11, ZSM-12, ZSM-22, ZSM-23, ZSM-35, ZSM-48, ZSM-50, or combinations thereof;
wherein the catalyst comprises ZSM-5;
wherein the catalyst composition comprises a crystalline molecular sieve characterized by an SAR from greater than 12 to 240 and a CI from 5 to 10;
wherein the catalyst in the fluidized bed comprises a catalytic molecular sieve and wherein the catalytic molecular sieve comprises from 30 to 90 percent by weight or 40 to 70 percent by weight of the composition of the catalyst particles;
wherein the catalyst in the fluidized bed is in the form of fluidizable microspheres;
wherein the product vapor mixture from the catalytic conversion comprises at least 20, or at least 30, or at least 50 mass % olefins, in some embodiments in the range of 20 to 90 mass % olefins;
wherein the mass yield of olefins in the product vapor mixture from the catalytic conversion is at least 30%, or at least 40%, or at least 45%, or at least 50%, or at least 55%, or at least 60%, or from 20% to 90%, or from 30% to 70%, or from 45% to 60%, olefins based on the mass of the polymer feed;
wherein the mass yield of BTX in the gaseous product mixture from the catalytic reactor is at least 5%, at least 10%, or at least 20%, or at least 30%, or at least 35%, or at least 40%, or from 1% to 90%, for from 5% to 70%, from 10% to 60%, or from 20% to 50%, BTX based on the mass of the polymer feed;
wherein the mass yield of olefins plus aromatics is greater than 40%, or greater than 60% or greater than 70%, or greater than 75%, or greater than 80%, or from 40% to 99%, or from 60% to 95%, or from 65% to 90%, and the mass yield of all products is no more than 100% based on the mass of solid hydrocarbonaceous materials fed to the process
wherein the vapor products of the catalytic pyrolysis are passed through one or more solids separation devices comprising one or more cyclones;
wherein the gaseous catalytic pyrolysis product mixture comprises CH4 and C2-C4 paraffins;
wherein the catalytic pyrolysis product vapor mixture is subjected to a separation process to produce a stream of gases enriched in CH4, CO, and H2; and passing at least a portion of the stream of gases enriched in CH4, CO, and H2 to the regenerator where they are combusted;
wherein the vapor products of the catalytic pyrolysis are passed to a separations and recovery facility;
wherein the product vapor mixture from the catalytic pyrolysis comprises at least 20, or at least 30, or at least 50 mass % olefins, or from 20 to 90 mass % olefins;
wherein the mass yield of olefins in the product vapor mixture from the catalytic pyrolysis is at least 30%, or at least 40%, or at least 45%, or at least 50%, or at least 55%, or at least 60%, or from 20% to 90%, or from 30% to 70%, or from 45% to 60%, olefins based on the mass of the polymer feed;
wherein the selectivity of ethylene as a percentage of the total olefins produced is at least 20%, or at least 25%, or at least 30%, or from 10% to 60%, or from 20% to 45%, or from 25% to 35%;
wherein selectivity of propylene as a percentage of the total olefins produced is at least 20%, or at least 30%, or at least 40%, or at least 45%, or at least 50%, or from 20% to 70%, or from 25% to 65%, or from 28% to 55%;
wherein benzene, toluene, xylenes, or a mixture of BTX is recovered from the product vapor mixture;
wherein the mass yield of BTX in the gaseous product mixture from the catalytic reactor is at least 5%, at least 10%, or at least 20%, or at least 30%, or at least 35%, or at least 40%, or from 1% to 90%, for from 5% to 70%, from 10% to 60%, or from 20% to 50%, BTX based on the mass of the polymer feed
wherein aromatics or olefins or both are recovered from the vapor products;
wherein at least a portion of the olefins recovered is recycled to the catalytic pyrolysis reactor;
wherein at least a portion of the C1-C4 hydrocarbons recovered is recycled to the oxidation reactor;
wherein at least a portion of the catalyst is removed from the catalytic pyrolysis reactor and regenerated by reaction with air or oxygen or an oxidizing gas in a catalyst regenerator and at least a portion of the regenerated catalyst is returned to the catalytic pyrolysis reactor;
wherein heat from the catalyst regenerator is provided to the plastic feed or to the catalytic pyrolysis reactor;
wherein the hot regenerated catalyst supplies heat to drive the catalytic pyrolysis process;
wherein catalyst recovered from the cyclones is fed to the regenerator;
wherein a portion of the energy generated in the catalyst regenerator can be used as thermal energy in the catalytic pyrolysis reactor, or for products separation, or both, or the energy can be converted to electrical energy, or the generated energy can be used as thermal energy and electrical energy within the plant or exported, or some combination thereof.
wherein the net movement of catalyst through the regenerator is in the upflow direction.
wherein the products of the catalytic pyrolysis are fed to the separations portion of a steam cracker or hydrocracker facility;
wherein the product mixture from the catalytic pyrolysis is passed to the separation train of a refinery or chemical plant;
wherein the steam cracker or hydrocracker is within a refinery;
wherein carbon oxides or water or both are at least partially removed from the products of the catalytic pyrolysis before the product mixture is fed to the separations portion of the steam cracker or hydrocracker;
wherein solids are removed from the products of the catalytic pyrolysis such that the solids content is less than 10, or less than 5, or less than 2, or less than 1 mg/m3 of product vapor before the product vapor is fed to the steam cracker or hydrocracker;
wherein at least a portion of the methane separated in the separation train of the steam cracker or hydrocracker is fed to the oxidation reactor;
wherein methane or ethane or C1-C4 alkanes separated in the separations portion of a steam cracker or hydrocracker are fed to the oxidation reactor;

wherein olefins or aromatics or both are recovered from the separations portion of the steam cracker or hydrocracker;

wherein the chlorine content of the vapor stream fed to the steam cracker or hydrocracker is less than 50, or 20, or 10, or 5, or 3, or 2, or 1, or from 0.1 to 50, or from 0.5 to 20, or from 1 to 5 ppm by weight.

wherein the plastic feed mixture is pretreated before being fed to the catalytic pyrolysis reactor;

wherein the plastic feed mixture is dried to achieve a moisture content of no more than 20, or 10, or 5 wt % moisture;

wherein the plastic feed is comminuted to particles no larger than 40, or 20, or 10, or 5, or 2, or 1 mm in their longest dimension;

wherein the plastic feed mixture is washed with water, or acid, or base, or by a sequence of more than one washing with one or more wash solutions;

wherein at least a portion of the chlorine-containing plastics are selectively removed from the feed mixture;

wherein the feed stream of plastics is first heated to at least 200° C. to achieve a molten state and filtered to remove solids;

wherein the plastic feed mixture is pretreated by pyrolyzing in a pyrolysis reactor by heating anaerobically to a temperature of between 250 and 300° C. to at least partially decompose the polymers;

wherein the pretreatment pyrolysis reactor is one or more moving bed, one-screw extruder, two screw extruder, auger reactor, rotating kiln reactor, or a stepped grate reactor, or some combination thereof;

wherein the pretreatment pyrolysis reactor comprises an inlet port and an exit port, the temperature can be from 20° C. to 150° C., such as 20 to 100° C., or 20 to 50° C., at or near the inlet port, and the range of temperature at the high temperature exit port can be from 150 C to 300° C., such as from 200 to 275° C., or from 225 to 250° C.;

wherein the pretreatment pyrolysis reactor comprises two or more reactors in series;

wherein the residence time of condensed phases in the pretreatment pyrolysis reactor, or in either reactor when there is more than one pyrolysis reactor, is at least 1, or at least 5, or at least 10, or at least 20, or at least 30, or from 1 to 60, or from 5 to 30, or from 10 to 30 minutes, wherein the feed is heated to a temperature greater than 150° C. in a pyrolysis reactor, the vapors are removed, and the condensed phases are passed to the catalytic pyrolysis reactor or to a second pyrolysis reactor;

wherein the chlorine content of the products of the pretreatment pyrolysis reactor is less than 50, or 20, or 10, or 5, or 2, or from 0.1 to 50, or from 0.5 to 20, or from 1 to 5 ppm by weight.

wherein a solid co-reactant material is fed to the pretreatment pyrolysis reactor;

wherein the solid co-reactant comprises one or more materials chosen from among agricultural lime, calcium oxide, calcium hydroxide, magnesium oxide, magnesium hydroxide, limestone, or hydrotalcites, or some combination thereof;

wherein the solid co-reactant material is separated from the products of the pretreatment pyrolysis and transferred to a combustion regenerator wherein the carbonaceous materials are reacted with air and at least a portion of the hot solid co-reactant material is returned to the pyrolysis reactor;

wherein the products produced in the pretreatment pyrolysis reactor are transferred, without cooling a significant portion of the products, to the catalytic pyrolysis reactor containing a catalyst;

wherein heat from the hot regenerated catalyst provides energy to the optional pretreatment process;

There are many advantages of chemically recycling plastics by pyrolysis in a catalytic pyrolysis reactor with the products of light alkane oxidation including: a mixture of any type of plastics is suitable, the plastic particles need not be ground to small size since the long residence time in the catalytic pyrolysis reactor or reactors ensures that the plastic pieces are heated to decomposition temperatures, the catalytic pyrolysis can be operated at high temperatures, vapor products from the alkane oxidation provide additional olefin to the catalytic pyrolysis reactor to increase aromatics yield, and energy can be captured from the oxidation of the light hydrocarbons for use in the process or for generating power.

GLOSSARY

Figure 1:
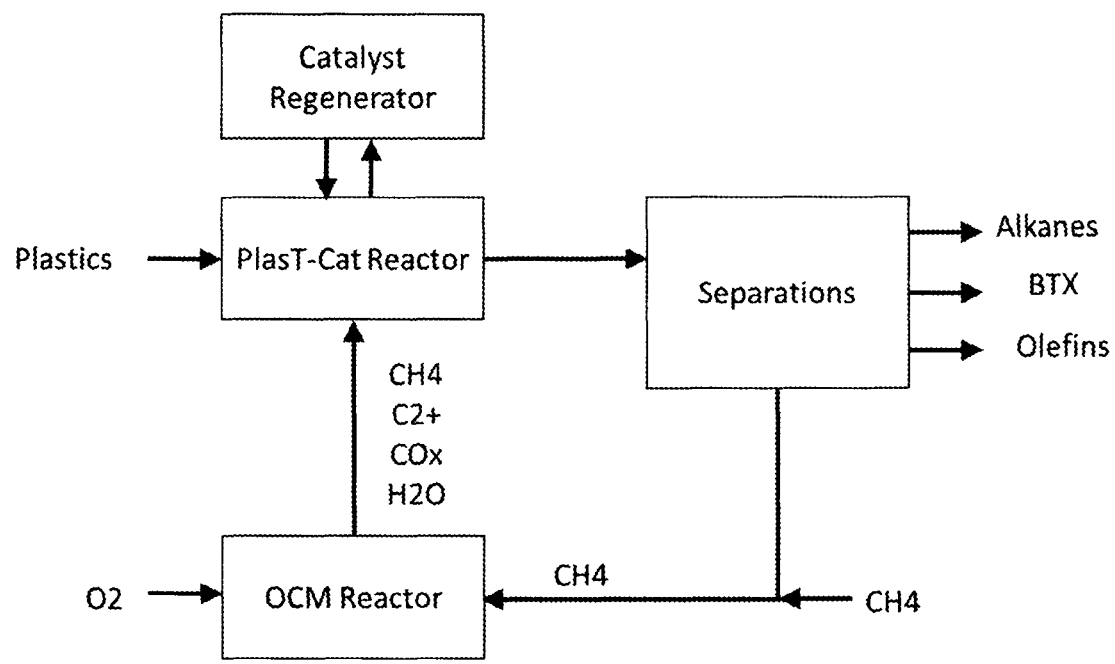
FIG. 1 presents a conceptual embodiment of the process for converting mixed plastic materials to valuable products by catalytically pyrolyzing the mixed plastics along with the vapor products of light alkane oxidation to produce olefins, aromatics, or some combination thereof.

Aromatics—As used herein, the terms "aromatics" or "aromatic compound" are used to refer to a hydrocarbon compound or compounds comprising one or more aromatic groups such as, for example, single aromatic ring systems (e.g., benzyl, phenyl, etc.) and fused polycyclic aromatic ring systems (e.g., naphthyl, 1,2,3,4-tetrahydronaphthyl, etc.). Examples of aromatic compounds include, but are not limited to, benzene, toluene, indane, indene, 2-ethyl toluene, 3-ethyl toluene, 4-ethyl toluene, trimethyl benzene (e.g., 1,3,5-trimethyl benzene, 1,2,4-trimethyl benzene, 1,2,3-trimethyl benzene, etc.), ethylbenzene, styrene, cumene, methylbenzene, propylbenzene, xylenes (e.g., p-xylene, m-xylene, o-xylene, etc.), naphthalene, methyl-naphthalene (e.g., 1-methyl naphthalene, anthracene, 9,10-dimethylanthracene, pyrene, phenanthrene, dimethyl-naphthalene (e.g., 1,5-dimethylnaphthalene, 1,6-dimethylnaphthalene, 2,5-dimethylnaphthalene, etc.), ethyl-naphthalene, hydrindene, methyl-hydrindene, and dymethyl-hydrindene. Single-ring and/or higher ring aromatics may also be produced in some embodiments.

Fluid—The term "fluid" refers to a gas, a liquid, a mixture of a gas and a liquid, or a gas or a liquid containing dispersed solids, liquid droplets and/or gaseous bubbles. The terms "gas" and "vapor" have the same meaning and are sometimes used interchangeably. In some embodiments, it may be advantageous to control the residence time of the fluidization fluid in the reactor. The fluidization residence time of the fluidization fluid is defined as the volume of the reactor divided by the volumetric flow rate of the fluidization fluid under process conditions of temperature and pressure.

Fluidized Bed Reactor—The term "fluidized bed reactor" is given its conventional meaning in the art and is used to refer to reactors comprising a vessel that can contain a granular solid material (e.g., silica particles, catalyst particles, etc.), in which a fluid (e.g., a gas or a liquid) is passed through the granular solid material at velocities sufficiently high as to suspend the solid material and cause it to behave as though it were a fluid. Examples of fluidized bed reactors are described in "Fluidization Engineering" by D. Kunii and O. Levenspiel, Butterworth-Heinemann, 1991, incorporated herein by reference. The term "circulating fluidized bed reactor" is also given its conventional meaning in the art and is used to refer to fluidized bed reactors in which the granular solid material is passed out of the reactor, circulated through a line in fluid communication with the reactor, and recycled back into the reactor. Examples of circulating fluidized bed reactors are described in "Fluidization Engineering" by D. Kunii and O. Levenspiel, Butterworth-Heinemann, 1991.

Bubbling fluidized bed reactors and turbulent fluidized bed reactors are also known to those skilled in the art. In bubbling fluidized bed reactors, the fluid stream used to fluidize the granular solid material is operated at a sufficiently low flow rate such that bubbles and voids are observed within the volume of the fluidized bed during operation. In turbulent fluidized bed reactors, the flow rate of the fluidizing stream is higher than that employed in a bubbling fluidized bed reactor, and hence, bubbles and voids are not observed within the volume of the fluidized bed during operation. Examples of bubbling and turbulent fluidized bed reactors are described in Kirk-Othmer Encyclopedia of Chemical Technology (online), Vol. 11, Hoboken, N.J.: Wiley-Interscience, 2001, pages 791-825, incorporated herein by reference.

Olefins—The terms "olefin" or "olefin compound" (a.k.a. "alkenes") are given their ordinary meaning in the art, and are used to refer to any unsaturated hydrocarbon containing one or more pairs of carbon atoms linked by a double bond. Olefins include both cyclic and acyclic (aliphatic) olefins, in which the double bond is located between carbon atoms forming part of a cyclic (closed-ring) or of an open-chain grouping, respectively. In addition, olefins may include any suitable number of double bonds (e.g., monoolefins, diolefins, triolefins, etc.). Examples of olefin compounds include, but are not limited to, ethene, propene, allene (propadiene), 1-butene, 2-butene, isobutene (2 methyl propene), butadiene, and isoprene, among others. Examples of cyclic olefins include cyclopentene, cyclohexane, cycloheptene, among others. Aromatic compounds such as toluene are not considered olefins; however, olefins that include aromatic moieties are considered olefins, for example, benzyl acrylate or styrene.

Catalysts—Catalyst components useful in the context of this invention can be selected from any catalyst known in the art, or as would be understood by those skilled in the art. Catalysts promote and/or affect reactions. Thus, as used herein, catalysts lower the activation energy (increase the rate) of a chemical process, and/or improve the distribution of products or intermediates in a chemical reaction (for example, a shape selective catalyst). Examples of reactions that can be catalyzed include: dehydration, dehydrogenation, isomerization, hydrogen transfer, hydrogenation, polymerization, cyclization, desulfurization, denitrogenation, deoxygenation, aromatization, decarbonylation, decarboxylation, aldol condensation, and combinations thereof. Catalyst components can be considered acidic, neutral or basic, as would be understood by those skilled in the art.

For catalytic pyrolysis, particularly advantageous catalysts include those containing internal porosity selected according to pore size (e.g., mesoporous and pore sizes typically associated with zeolites), e.g., average pore sizes of less than about 10 nm, less than about 5 nm, less than about 2 nm, less than about 1 nm, less than about 0.5 nm, or smaller. In some embodiments, catalysts with average pore sizes of from about 0.5 nm to about 10 nm may be used. In some embodiments, catalysts with average pore sizes of between about 0.55 nm and about 0.65 nm, or between about 0.59 nm and about 0.63 nm may be used. In some cases, catalysts with average pore sizes of between about 0.7 nm and about 0.8 nm, or between about 0.72 nm and about 0.78 nm may be used.

In some preferred embodiments of catalytic pyrolysis, the catalyst may be selected from naturally occurring zeolites, synthetic zeolites and combinations thereof. In certain embodiments, the catalyst may be a ZSM-5 zeolite catalyst, as would be understood by those skilled in the art. Optionally, such a catalyst can comprise acidic sites. Other types of zeolite catalysts include: ferrierite, zeolite Y, zeolite beta, mordenite, MCM-22, ZSM-23, ZSM-57, SUZ-4, EU-1, ZSM-11, (S)AlPO-31, SSZ-23, among others. Zeolites and other small pore materials are often characterized by their Constraint Index. The Constraint Index approximates the ratio of the cracking rate constants for normal hexane and 3-methylpentane. The method by which Constraint Index is determined is described more fully in U.S. Pat. No. 4,029,716, incorporated by reference for details of the method. Zeolites mentioned in this disclosure are at least partially in their protonated form wherein the cations in the structure have been at least partially substituted with H+ ions.

Constraint Index (CI) values for some typical materials are:

TABLE 1

Constraint Indices of some common zeolites.

| Material | Constraint Index | Test Temp, ° C. |
| --- | --- | --- |
| ZSM-4 | 0.5 | 316 |
| ZSM-5 | 6-8.3 | 371-316 |
| ZSM-11 | 5-8.7 | 371-316 |
| ZSM-12 | 2.3 | 316 |
| ZSM-20 | 0.5 | 371 |
| ZSM-22 | 7.3 | 427 |
| ZSM-23 | 9.1 | 427 |
| ZSM-34 | 50 | 371 |
| ZSM-35 | 4.5 | 454 |
| ZSM-48 | 3.5 | 538 |
| ZSM-50 | 2.1 | 427 |
| Mordenite | 0.5 | 316 |
| REY | 0.4 | 316 |
| Dealuminized Y | 0.5 | 510 |
| Beta | 0.6-2 | 316-399 |

The CI may vary within the indicated range of 1 to 12. Likewise, other variables such as crystal size or the presence of possibly occluded contaminants and binders intimately combined with the crystal may affect the CI. It is understood to those skilled in the art that the CI, as utilized herein, while affording a highly useful means for characterizing the molecular sieves of interest is approximate, taking into consideration the manner of its determination, with the possibility, in some instances, of compounding variable extremes. However, the CI will have a value for any given molecular sieve useful herein within the approximate range of 1 to 12.

In other embodiments, non-zeolite catalysts may be used; for example, WOx/ZrO2, aluminum phosphates, etc. In some embodiments, the catalyst may comprise a metal and/or a metal oxide. Suitable metals and/or oxides include, for example, nickel, palladium, platinum, titanium, vanadium, chromium, manganese, iron, cobalt, zinc, copper, gallium, and/or any of their oxides, among others. In some cases promoter elements chosen from among the rare earth elements, i.e., elements 57-71, cerium, zirconium or their oxides for combinations of these may be included to modify activity or structure of the catalyst. In addition, in some cases, properties of the catalysts (e.g., pore structure, type and/or number of acid sites, etc.) may be chosen to selectively produce a desired product.

Plastics or Polymers—The terms "plastics" and "polymers" are used interchangeably herein. A polymer is a carbon-based (at least 50 mass % C) material chiefly made up of repeating units and having a number average molecular weight of at least 100, typically greater than 1000 or greater than 10,000. Polymers include thermoplastic polymers such as, for example, polyethylene, polypropylene, polyesters, polyethylene terephthalate (PET), acrylonitrile-butadiene-styrene (ABS) copolymers, polyamide, polyurethane, polyethers, polycarbonates, poly(oxides), poly(sulfides), polyarylates, polyetherketones, polyetherimides, polysulfones, polyurethanes, polyvinyl alcohols, and polymers produced by polymerization of monomers, such as, for example, dienes, olefins, styrenes, acrylates, acrylonitrile, methacrylates, methacrylonitrile, diacids and diols, lactones, diacids and diamines, lactams, vinyl halides, vinyl esters, block copolymers thereof, and alloys thereof, thermoset polymers such as, for example, epoxy resins; phenolic resins; melamine resins; alkyd resins; vinyl ester resins; unsaturated polyester resins; crosslinked polyurethanes; polyisocyanurates; crosslinked elastomers, including but not limited to, polyisoprene, polybutadiene, styrene-butadiene, styrene-isoprene, ethylene-propylene-diene monomer polymer; and blends thereof. Mixtures of polymers separated from municipal solid waste or other waste streams are suitable feeds provided they contain only small fractions of contaminants such as S, N, O, or halogens. Polymers yielding halogenated material upon pyrolysis, for example, polyvinyl chloride (PVC), polytetrafluoroethylene (PTFE), and other halogenated polymers, are generally minimized or excluded from the feed materials useful in this invention.

Pyrolysis—The terms "pyrolysis" and "pyrolyzing" are given their conventional meaning in the art and are used to refer to the transformation of a compound, e.g., a solid hydrocarbonaceous material, into one or more other substances, e.g., volatile organic compounds, gases and coke, by heat, preferably without the addition of, or in the absence of, $O_2$. Preferably, the volume fraction of $O_2$ present in a pyrolysis reaction chamber is 0.5% or less. Pyrolysis may take place with or without the use of a catalyst. "Catalytic pyrolysis" refers to pyrolysis performed in the presence of a catalyst, and may involve steps as described in more detail below. Example of catalytic pyrolysis processes are outlined, for example, in Huber, G. W. et al, "Synthesis of Transportation Fuels from Biomass: Chemistry, Catalysts, and Engineering," Chem. Rev. 106, (2006), pp. 4044-4098.

Residence Time—As used in this disclosure, the term 'residence time' of a material in a device or reactor can be calculated by dividing the volume of the device or reactor by the volumetric feed rate of the feed material. For example, if the flow of fluidization gas into a reactor is 5 SLPM (standard liters per minute) and the reactor volume is 2 liters, the residence time is 2/5=0.4 minutes at standard conditions. The residence time is often adjusted to reaction conditions by including the expansion or contraction due to the temperature difference; this is significant for gases, but is often insignificant and therefore ignored for liquids and solids.

Selectivity—The term "selectivity" refers to the amount of production of a particular product in comparison to a selection of products. Selectivity to a product may be calculated by dividing the amount of the particular product by the amount of a number of products produced. For example, if 75 grams of aromatics are produced in a reaction and 20 grams of benzene are found in these aromatics, the selectivity to benzene amongst aromatic products is 20/75=26.7%. Selectivity can be calculated on a mass basis, as in the aforementioned example, or it can be calculated on a carbon basis, where the selectivity is calculated by dividing the amount of carbon that is found in a particular product by the amount of carbon that is found in a selection of products. Unless specified otherwise, for reactions involving polymers as reactants, selectivity is on a mass basis. For reactions involving conversion of a specific molecular reactant (ethene, for example), selectivity is the percentage (on a mass basis unless specified otherwise) of a selected product divided by all the products produced.

Yield—The term yield is used herein to refer to the amount of a product flowing out of a reactor divided by the amount of reactant flowing into the reactor, usually expressed as a percentage or fraction. Yields are often calculated on a mass basis, carbon basis, or on the basis of a particular feed component. Mass yield is the mass of a particular product divided by the mass of feed used to prepare that product. For example, if 500 grams of polymer is fed to a reactor and 45 grams of benzene is produced, the mass yield of benzene would be 45/500=9% benzene. Carbon yield is the mass of carbon found in a particular product divided by the mass of carbon in the feed to the reactor. For example, if 500 grams of polymer that contains 90% carbon is reacted to produce 400 grams of benzene that contains 92.3% carbon, the carbon yield is [(400*0.923)/(500*0.90)] =82.0%.

As is standard patent terminology, the term "comprising" means "including" and does not exclude additional components. Any of the inventive aspects described in conjunction with the term "comprising" also include narrower embodiments in which the term "comprising" is replaced by the narrower terms "consisting essentially of" or "consisting of." As used in this specification, the terms "includes" or "including" should not be read as limiting the invention but, rather, listing exemplary components.

DETAILED DESCRIPTION OF THE INVENTION

Producing value from waste streams is becoming more urgent as the world aims to develop a circular economy that is designed to minimize resource input, as well as waste and emissions production. Circular economy aims to reach the maximum efficiency in the use of finite resources, a gradual transition to renewable resources, and recovery of the materials and products at the end of their useful life. The process of the present disclosure enables the circular economy by recovering the value in waste plastics and light hydrocarbons. The disclosed process includes the catalytic pyrolysis of a waste plastics mixture to which the products of the partial oxidation of methane or other light hydrocarbons have been added.

Monetizing methane by upgrading processes has long been a goal of the chemical and petroleum industries. Despite extensive study, oxidative methane coupling to produce C2+ hydrocarbons has failed to become a stand-alone commercial process due to the fundamental limitations of the chemistry. The reaction is a radical reaction wherein the products, ethane and ethylene, are about as susceptible to conversion as is methane. A maximum yield is reached beyond which product destruction exceeds product formation. The maximum yield is about 35% yield (Bhatia, S., et al, "Oxidative coupling of methane (OCM) in a catalytic membrane reactor and comparison of its performance with other catalytic reactors," Chem Eng. J., 148 (2-3), 2009, 525-532) that is far below the roughly 65% yield required to support a stand-alone process. The low yield and high costs of the separation of the C2+ products from the product mixture accounts for the high cost of the process.

The present disclosure provides a process in which the oxidative coupling of methane can be integrated with the catalytic pyrolysis of plastics so that the olefins and the heat produced in the oxidative coupling are utilized efficiently to 1) provide the heat required for the catalytic pyrolysis, 2) increase the yield of aromatics and olefins from the catalytic pyrolysis, and 3) take advantage of the economies of scale available with large capacity product separations facilities such as those associated with an existing steam cracker or hydrocracker.

FIG. 1 presents a conceptual embodiment of the process for converting mixed plastic materials to valuable products by catalytically pyrolyzing the mixed plastics along with the vapor products of light alkane oxidation to produce olefins, aromatics, or some combination thereof. A mixture of plastics is introduced into a catalytic fluid bed reactor (PlasT-Cat™) fitted with a catalyst for the conversion of polymers to olefins, alkanes, and aromatics. Methane, or a mixture of light C1-C4 hydrocarbons, is introduced into a partial oxidation reactor with an oxidant such as O2 or air. In the oxidation reactor (OCM, oxidative coupling of methane) the methane or mixed hydrocarbons react to form C2+ hydrocarbons comprising ethylene, as well as COx and steam. The hot gaseous product mixture is fed to the catalytic pyrolysis reactor providing heat to raise the temperature of the mixture to temperatures at which the polymers decompose and react in the presence of a catalyst to form olefins, aromatics, and alkanes. The products of the catalytic pyrolysis are passed to a separations train to recover BTX (benzene, toluene, xylenes), olefins, and other useful products. A portion of the methane or other light alkanes separated in the separations train can be used as the feed to the oxidation reactor, or methane from sources such as natural gas or biogas can be used. Coke or other materials that deposit on the catalyst are removed by passing a at least a portion of the catalyst to a catalyst regenerator wherein the materials are oxidized by air or other oxygen-containing gas to remove carbonaceous deposits and restore catalyst activity. At least a portion of the regenerated catalyst is returned to the fluidized bed PlasT-Cat™ reactor.

Figure 2:
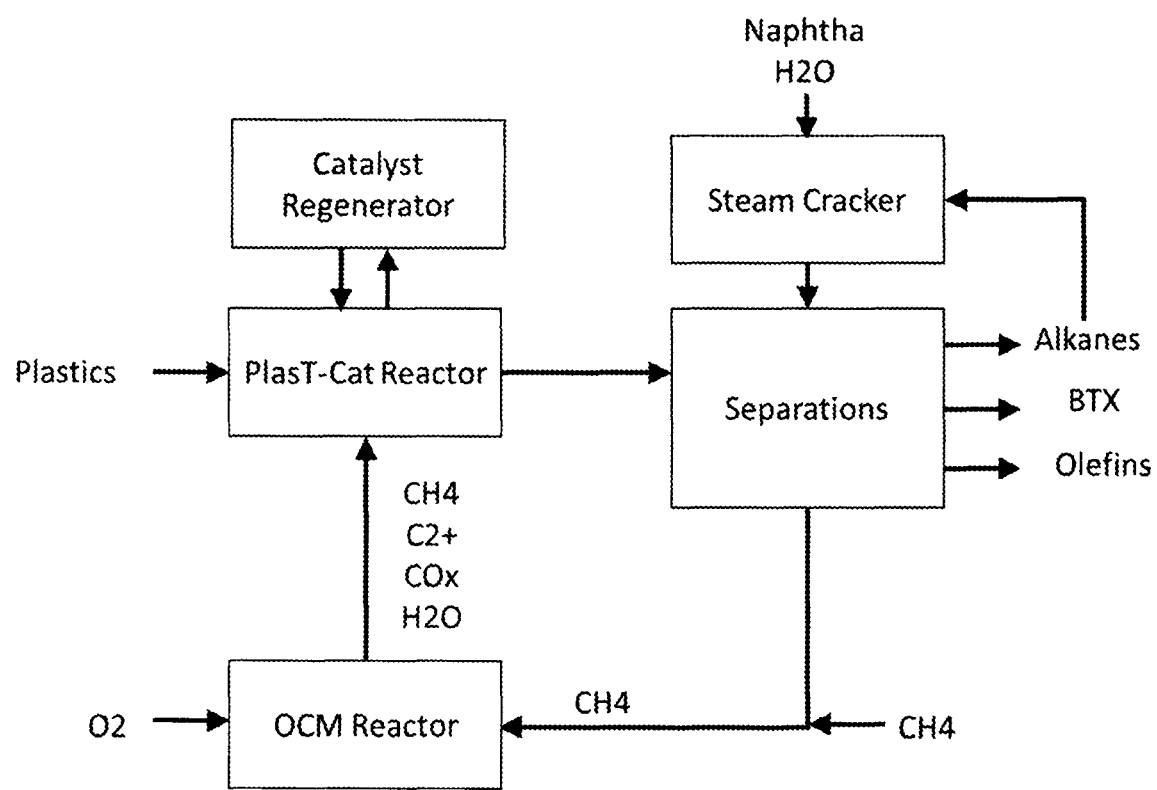
FIG. 2 depicts an embodiment of the disclosure in which the plastics and alkane upgrading process is integrated with a steam cracker.

FIG. 2 depicts an embodiment of the disclosure in which the plastics and alkane upgrading process is integrated with a steam cracker. In this arrangement, the products of the PlasT-Cat™ reactor are passed to the separations system of a steam cracker. Aromatics (BTX), olefins, and alkanes may be recovered from the separations system and a portion of the alkanes can be returned to the steam cracker for further processing. A portion of the methane or light hydrocarbon mixture may be fed to the oxidation reactor for conversion to additional ethylene and other products. Methane from external sources may optionally be added to the feed to the oxidation reactor. In this embodiment the decomposed plastics and a portion of the light hydrocarbons are introduced into the existing steam cracking facility to increase the production of chemicals or fuels. In an alternative (not shown in FIG. 2), products from the OCM reactor can be feed to a pyrolysis reactor upstream of the PlasT-Cat™ Reactor.

Figure 3:
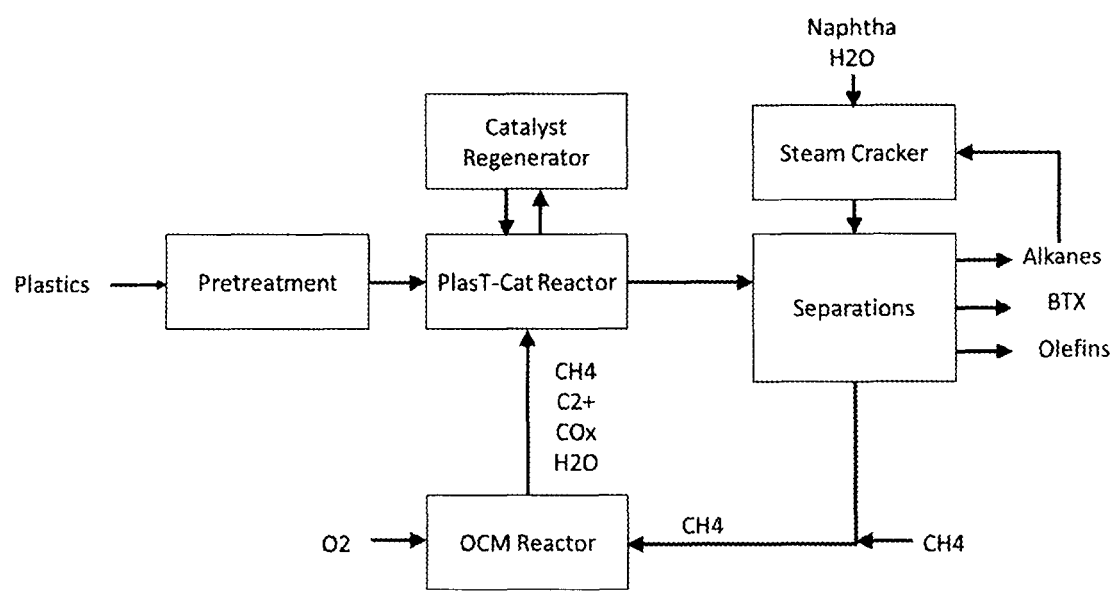
FIG. 3 presents another embodiment of the disclosure in which the plastics mixture is first pretreated before introduction into the catalytic pyrolysis reactor.

FIG. 3 presents another embodiment of the disclosure in which the plastics mixture is first pretreated before introduction into the PlasT-Cat™ reactor. Pretreatment of the plastics mixture may remove chlorine-containing materials by driving off HCl, or melting the plastics to allow for the separation of solids therefrom, or washing the plastics to remove impurities such as salts, metals, mineral matter, or dirt, or otherwise preparing the plastic mixture for processing by PlasT-Cat™.

The feed materials suitable for use in the invention can comprise all types of polymeric materials including polyethylene (PE), polypropylene (PP), polyacetylene, polybutylene, polyolefins, polyethylene terephthalate (PET), polybutylene terephthalate, polyester, copolyesters, polycarbonate, polyurethanes, polyamides, polystyrene (PS), polyacetal, epoxies, polycyanurates, polyacrylics, polyurea, vinyl esters, polyacrylonitrile, polyamide, polyurethane, polyethers, polycarbonates, poly(oxides), poly(sulfides), polyarylates, polyetherketones, polyetherimides, polysulfones, polyurethanes, polyvinyl alcohol, polyvinylchloride (PVC), polyvinyl dichloride (PVDC), polyvinyl acetate, nylon, copolymers such as ethylene-propylene, acrylonitrile-butadiene-styrene (ABS), nitrile rubber, natural and synthetic rubber, tires, styrene-butadiene, styrene-acrylonitrile, styrene-isoprene, styrene-maleic anhydride, ethylene-vinyl acetate, nylon 12/6/66, filled polymers, polymer composites, plastic alloys, other polymeric materials, and polymers or plastics dissolved in a solvent, whether obtained from polymer or plastic manufacturing processes as waste or discarded materials, post-consumer recycled polymer materials, materials separated from waste streams such as municipal solid waste, and polymers produced by polymerization of monomers, such as, for example, dienes, olefins, styrenes, acrylates, acrylonitrile, methacrylates, methacrylonitrile, diacids and diols, lactones, diacids and diamines, lactams, vinyl esters, block copolymers thereof, and alloys thereof; thermoset polymers such as, for example, epoxy resins; phenolic resins; melamine resins; alkyd resins; vinyl ester resins; unsaturated polyester resins; crosslinked polyurethanes; polyisocyanurates; crosslinked elastomers, including but not limited to, polyisoprene, polybutadiene, styrene-butadiene, styrene-isoprene, or some combination of these. The invention includes subcombinations of these materials, as desired, or as available from a particular location; the invention can be described as comprising one or any combination of these materials.

In any of the methods, the catalytic reactor can be a fluidized bed reactor; wherein the catalyst is a solid catalyst and the step of catalytically pyrolyzing comprises pyrolyzing in the presence of the solid catalyst in a fluidized bed reactor to produce a fluid product stream and used catalyst with coke; and wherein at least a portion of the carbon in the feed is converted to coke and volatile products. In any of the methods the vapors exiting the catalytic pyrolysis reactor can be passed through an optional solids separation device such as a cyclone or screen to remove entrained solids. In any of the methods at least a portion of the used catalyst with coke is transferred to a regenerator where the coke is reacted with oxygen or air to form hot regenerated catalyst, at least a portion of the hot regenerated catalyst is returned to the fluidized bed reactor, wherein heat from the hot regenerated catalyst provides energy to the step of pyrolyzing.

In any of the methods, the step of catalytically pyrolyzing may comprise pyrolysis in the presence of a fluid bed catalyst. The catalytic pyrolysis reactor may comprise a fluidized bed, circulating bed, bubbling bed, or riser reactor operating at a temperature in the range from 300° C. to 800° C., or from 350° C. to 750° C., or from 400° C. to 700° C., or from 450° C. to 650° C., or from 500° C. to 600° C. The residence time of the vapors in the catalytic pyrolysis can be from 1 second to 480 seconds, or from 1 second to 240 seconds, or from 2 seconds to 60 seconds, or from 3 seconds to 30 seconds, or from 4 seconds to 15 seconds. The pressure of the catalytic pyrolysis reactor can be at least 0.1 MPa (1 bara), or at least 0.3 MPa (3bara), or at least 0.4 MPa (4 bara), or from 0.1 to 2.0 MPa (1 to 20 bara), or from 0.1 to 1.0 MPa (1 to 10 bara), or from 0.3 to 0.8 MPa (3 to 8 bara), preferably from 0.4 to 0.6 MPa (4 to 6 bara), pressures are absolute pressures.

Design and conditions of the fluidized bed reactor can be those conventionally known. A fluidization gas may be needed at start-up; during steady-state operation, fluidization gas may comprise a portion of the vapor stream that, optionally, can be piped into the bottom of the fast catalytic pyrolysis fluidized bed reactor. Recycle gas from the process may be used as fluidizing gas or at least a portion of the product gas from the oxidation reactor may be used as a component of the fluidizing gas.

For catalytic pyrolysis, useful catalysts include those containing internal porosity selected according to pore size (e.g., mesoporous and pore sizes typically associated with zeolites), e.g., average pore sizes of less than 10 nm, less than 5 nm, less than 2 nm, less than 1 nm, less than 0.5 nm, or smaller. In some embodiments, catalysts with average pore sizes of from 0.5 to 10 nm may be used. In some embodiments, catalysts with average pore sizes of between 0.5 and 0.65 nm, or between 0.59 and 0.63 nm may be used. In some cases, catalysts with average pore sizes of between 0.7 and 0.8 nm, or between 0.72 and 0.78 nm may be used.

The catalyst composition particularly advantageous in the catalytic pyrolysis fluidized bed reactor of the present invention comprises a crystalline molecular sieve characterized by an SAR (silica to alumina, $SiO_2:Al_2O_3$ mass ratio) greater than 12, or from 12 to 240, and a CI (constraint index) from 1 to 12. Non-limiting examples of these crystalline molecular sieves are those having the structure of ZSM-5, ZSM-11, ZSM-12, ZSM-22, ZSM-23, ZSM-35, ZSM-48, ZSM-50, or combinations thereof. As an embodiment, the catalyst composition comprises a crystalline molecular sieve characterized by an SAR from greater than 12 to 240 and a CI from 5 to 10, such as, for example, molecular sieves having the structure of ZSM-5, ZSM-11, ZSM-22, ZSM-23 or combinations thereof. The method by which CI is determined is described more fully in U.S. Pat. No. 4,029,716, incorporated herein by reference for details of the method.

The molecular sieve for use herein or the catalyst composition comprising same may be thermally treated at high temperatures. This thermal treatment is generally performed by heating at a temperature of at least 370° C. for at least 1 minute and generally not longer than 20 hours (typically in an oxygen containing atmosphere, preferably air). While subatmospheric pressure can be employed for the thermal treatment, atmospheric pressure is desired for reasons of convenience. The thermal treatment can be performed at a temperature up to about 925° C. The thermally treated product is particularly useful in the present process.

For the catalyst compositions useful in this invention, the suitable molecular sieve may be employed in combination with a support or binder material such as, for example, a porous inorganic oxide support or a clay binder. Non-limiting examples of such binder materials include alumina, zirconia, silica, magnesia, thoria, titania, boria, and combinations thereof, generally in the form of dried inorganic oxide gels and gelatinous precipitates. Suitable clay materials include, by way of example, bentonite, kieselguhr, and combinations thereof. The relative proportion of suitable crystalline molecular sieve of the total catalyst composition may vary widely with the molecular sieve content ranging from 30 to 90 percent by weight and more usually in the range of 40 to 70 percent by weight of the composition. The catalyst composition may be in the form of an extrudate, beads or fluidizable microspheres.

The molecular sieve for use herein or the catalyst composition comprising it may have original cations replaced, in accordance with techniques well known in the art, at least in part, by ion exchange with hydrogen, or hydrogen precursor cations, or non-noble metal ions of Group VIII of the Periodic Table, i.e., nickel, iron or cobalt, or zinc, or gallium, or combinations thereof.

In any of the methods the vapors exiting the catalytic pyrolysis reactor can be passed through an optional solids separation device such as one or more cyclones or screens to remove entrained solids. A solid mixture comprising deactivated catalyst may comprise residual carbon and/or coke as well as coke or char from the process, which may be removed via reaction with the oxidizing agent in the regenerator. In any of the methods catalyst may be withdrawn from the catalytic pyrolysis reactor and sent to a catalyst regenerator where it is reacted with an oxygen containing gas and regenerated catalyst may be returned to the catalytic pyrolysis reactor. The oxygen containing gas may originate from any source including, for example, a tank of oxygen, atmospheric air, steam, among others. In the regenerator, the catalyst is re-activated by reacting the catalyst with the oxidizing agent and heat is generated. In some embodiments a portion of the gaseous products from the catalytic pyrolysis process is fed to the catalyst regenerator to be combusted with the solid materials. The gaseous products may be first separated into an olefin rich stream and an olefin poor stream and at least a portion of the olefin poor stream may be fed to the catalyst regenerator. In processes in which catalyst from the catalytic pyrolysis is regenerated, heat that is generated by the oxidation of coke, char, and other materials in a catalyst regenerator may be used elsewhere in the process, or for conversion to electricity for export.

In some embodiments, for example when recycled polymeric materials are used, impurities may optionally be removed from the feed composition prior to being fed to the catalytic pyrolysis reactor, e.g., by an optional pretreatment step such as in FIG. 3. In any of the methods wherein feed is pretreated to remove impurities by washing, the washing solution or solutions can be acidic, basic, or nearly neutral. The washing sequence may comprise one contact with a wash solution or numerous contacts with washing solution, and the washing solutions may be different in different steps in the washing sequence. The washing may be conducted in a countercurrent fashion or in a series of batch contacting reactors.

In some instances, the pretreatment step may include mechanical separation, sink/float separation, air elutriation, or other known separation processes, preferably in an automated mode. In some instances, the particle size of the solid polymer feed composition may be reduced in a size reduction system prior to passing the feed to the pyrolysis reactor. In some embodiments, the average diameter of the reduced size feed composition exiting the size reduction system may comprise no more than about 50%, not more than about 25%, no more than about 10%, no more than about 5%, no more than about 2% of the mass average diameter of the feed composition fed to the size reduction system. The feed mixture may comprise plastics mixtures in which at least 85% by mass, or at least 90% by mass, or at least 95% by mass of the particles pass through a 0.25 inch (0.6 cm), or 0.5 inch (1.2 cm), or 1.0 inch (2.5 cm), or 1.5 inch (3.7 cm), or 2 inch (5.0 cm), or 4 inch (10.0 cm) screen. Average diameter (size) can be measured by sieving through mesh (screen). Large-particle feed material may be more easily transportable and less difficult to process than small-particle feed material. On the other hand, in some cases it may be advantageous to feed small particles to the reactor. The use of a size reduction system allows for the transport of large-particle feed between the source and the process, while enabling the feed of small particles to the reactor.

In any of the methods, wherein feed is pretreated in a pyrolysis reactor or reactors, any of the reactors can be a moving bed reactor wherein the feed material is impelled along the length of the reactor by mechanical or gravitational means or both mechanical and gravitational means. Typical examples of reactors suitable for the pyrolysis reactor include a 1-screw extruder, 2-screw extruder, auger reactor, rotating kiln reactor, or stepped grate reactor. In any of the embodiments the pyrolysis reactor may be fitted with a means of separating condensed materials such as solids or liquids or both from vapor products and an outlet for the condensed phases separate from the outlet for the vapor phase. In any of the embodiments the pyrolysis reactor may have multiple heating zones with successively higher temperatures in later zones. In some embodiments the pyrolysis reactor is fitted with a gas outlet at an area of the reactor where the temperature of the materials in the reactor is less than 300° C. or between 250 C and 300° C. to allow for the removal of products produced at low temperatures such as steam, HCl, NH3, or other materials from the reactor. In one embodiment a separating barrier is fitted within the pyrolysis reactor immediately downstream of the gas outlet to at least partially prevent gases evolved at low temperature from passing along with the molten and solid materials into the hotter portions of the reactor.

Where an auger reactor is utilized, embodiments of this invention include helical augers that optionally have different pitch dimensions at different portions of the auger to adjust the velocity of the condensed phases from the entry to the exit of the reactor. In this embodiment the flight thickness and shaft diameter may also be of variable dimension along the length of the auger to control the flow velocity of the vapor and condensed phases. Augers with paddles, or cuts, or folded flights are also envisioned as within the scope of these embodiments.

In embodiments wherein a rotating kiln reactor is utilized, the kiln cylinder can be fitted with lifters, such as helical lifters attached to the cylinder wall or tabular lifters, folded lifters, or segmented lifters extending from the cylinder wall. A rotating kiln reactor can also be inclined either up or down towards the exit end of the kiln depending on the desired residence time and flow velocity desired for the condensed phases within the kiln, thus taking advantage of gravity to control residence time of the condensed phases. It is also envisioned that the rotation rate of the rotating kiln reactor can be adjusted as desired, for example between 20 revolutions per minute to 0.2 revolution per minute depending on the nature of the feed mixture and the co-reactant added in order to provide thorough mixing and high heat transfer. A rotating kiln reactor can be heated externally with combustion of waste process gases such as $CH_4$, $C2$-$C4$ paraffins, $H_2$, $CO$, and the like recycled from the product separation or natural gas or electrically.

In any of the embodiments, the temperature profile within the pretreatment pyrolysis reactor can range from a lower temperature near the feed entry port to a higher temperature at the exit port or ports. The range of temperatures in the pretreatment pyrolysis reactor can be from 20° C. to 150° C., such as 20 to 100° C., or 20 to 50° C., at or near the inlet port, and the range of temperatures at the high temperature exit port can be from 150 C to 300° C., such as from 200 to 275° C., or from 225 to 250° C.

In embodiments wherein a solid co-reactant is fed to the pretreatment pyrolysis reactor the solid co-reactant material is optionally transferred to a combustion regenerator wherein the carbonaceous materials are reacted with air and at least a portion of the hot solid co-reactant material is returned to the pyrolysis reactor. In one embodiment of the invention the hot flue gas exiting the solid co-reactant regenerator is passed to a catalyst heater to heat the catalyst for the catalytic pyrolysis reactor.

EXAMPLES

Figure 4:
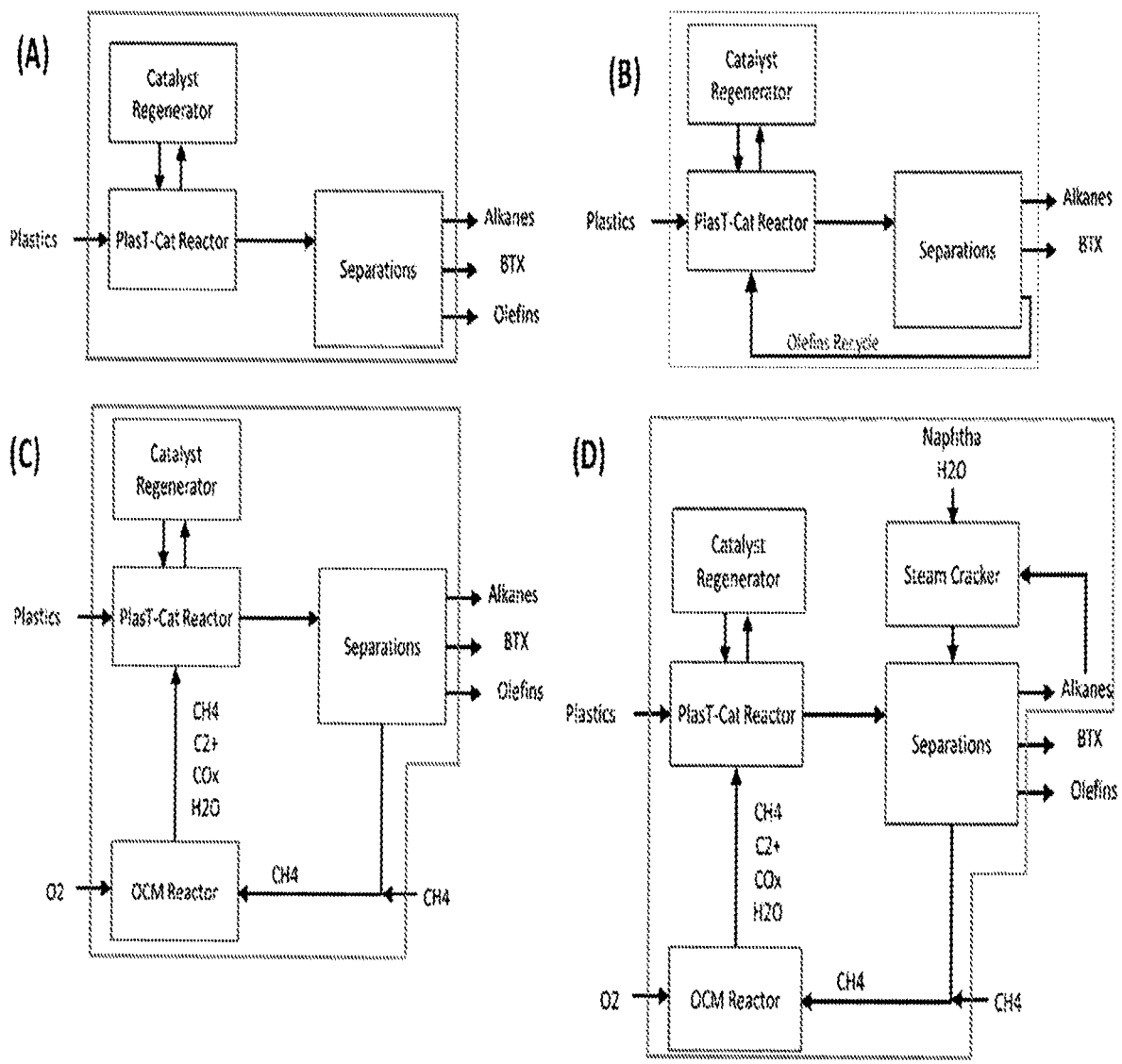
FIG. 4 presents four different embodiments of the process with different recycle schemes.

The calculated performance of the proposed configuration has been compared to the performance of the direct pass PlasTCat process as shown in FIG. 4. In FIG. 4, Scheme (A) depicts the direct pass process consisting of the catalytic pyrolysis reactor (PlasTCat) from which the products enter a separation section to separate alkanes, BTX and olefins. Scheme (B) depicts the configuration in which an olefins rich stream is separated from the reactor effluent and recycled back to the pyrolysis reactor. Schemes (C) and (D) depict two possible configurations of the integration of the alkane oxidation process into the system.

The performance of the alkane oxidation reactor was determined based on the literature experimental data of: Mleczko, L., Gayko, G., Niemi, V. M., & Hiltunen, J. (1997, *"Reaction engineering studies in a polytropic fixed-bed reactor over a highly active and selective catalyst for oxidative methane coupling"*, Chemical Engineering & Technology: Industrial Chemistry-Plant Equipment-Process Engineering-Biotechnology, 20(1), 29-35), in which the following parameters were defined: $CH_4$ to $O_2$ ratio at the inlet=2.2, the conversion of $O_2$=98.3%, conversion of $CH_4$=40.8%, carbon selectivity towards $C_{2+}$ hydrocarbons=52.5%, ratio of olefinic to paraffinic $C_2$ products=1.21, yield of hydrogen—1.9 wt %, yield of $C_{2+}$ hydrocarbons=21.4 wt %. The alkane oxidation reactor was set at operating conditions of 840° C. and 4 bar; a 20% reduction in $C_{2+}$ selectivity was included as a correction factor to account for operating at 4 bar, based on the experimental data reported by Zavyalova, Ulyana, et al. *"Statistical analysis of past catalytic data on oxidative methane coupling for new insights into the composition of high-performance catalysts."* ChemCatChem 3.12 (2011): 1935-1947.

Based on these parameters a mass balance around the OCM reactor was performed as summarized in Table 2 for the base case, Scheme A. The configurations without alkane oxidation (A and B) were compared to those with alkane oxidation (C and D) based on the expected change in product yields of olefins and aromatics, in addition to the effect on the PlasTCat reactor and catalyst regenerator heat balance.

In order to assess the effect on the overall process yield, the kinetic behavior of the PlasT-Cat reactor has to be evaluated for the two cases. The PlasT-Cat reactor performance is assessed using a fluidized bed model combining both hydrodynamic and kinetic behaviors. The model is a compartment type model, as has been discussed extensively in the literature, and widely applied by practitioners in the field; details of such similar models have been described in detail in many sources, such as: Kato, K., and C. Y. Wen. "Bubble assemblage model for fluidized bed catalytic reactors." Chemical Engineering Science 24.8 (1969): 1351-1369. The premise of this model lies in capturing variations in hydrodynamic behaviors and species compositions at different entrance points of a multiphase fluidized bed reactor. The variability of these features is captured by axially dividing the reactor into compartments; the height of each compartment is equal to the average bubble size at the axial distance from the distributor. Each compartment consists of 2 or 3 phases, typically the bubble phase, the emulsion phase and the cloud phase. The bubble phase represents the volume of species existing as bubbles and is used to primarily capture the hydrodynamic behavior of the fluidized bed. The emulsion phase consists of species existing outside the bubble phase, and is used to capture non-hydrodynamic behaviors such as mass and heat transfer and reaction kinetics. Exchange between the phases occurs due to the bubble coalescence and breakup behavior along the axial distance of the reactor. In some cases, an additional cloud phase is included; this cloud phase is primarily used to act as a buffer region between the two other phases, primarily for mass transfer representation. Each compartment is then modeled as a perfectly mixed reactor, and interchange due to mass transfer, bubble coalescence/breakup and reactions occurs within subsequent compartments. Such a model was developed for the purposes of representing the PlasT-Cat reactor; hydrodynamic correlations were obtained from the literature to represent the bubble growth, bubble coalescence and breakup and mass interchange rates, whereas an empirical lumped kinetic model was used to represent the reaction kinetics. The kinetic model was developed based on an extensive experimental program to determine the catalytic pyrolysis performance of the PlasT-Cat system.

The PlasTCat reactor modeled in this example is at 570° C. and pressure of 4 bar, with an inlet fluidization velocity of 0.15 m/s, the reactor H/D is in the range of 1-2. For the single pass case, the composition of the fluidization gas into the reactor was taken to be inert. For the olefins recycle case, the composition of the recycle gas was taken to be 3.3% CO, 8.8% CO2, 2.73% H2, 15.82% Nitrogen, 0.88% Water, 7.67% paraffins, and 60.8% olefins, which was obtained experimentally. For the alkane oxidation case, the composition of the fluidization gas into the reactor had the same composition as the gas exiting the OCM reactor: 31.16% $CH_4$, 0.81% $O_2$. 5.58% $C_{2+}$ olefins, 4.61% $C_{2+}$ paraffins, 30.09% $CO_2$ and 27.78% $H_2O$. In both cases the plastic feed into the reactor consisted of 55.3% polyolefins, 17% polystyrene, 10% PET, 11% Nylon and the balance distributed between ABS, PMMA and biomass. The composition of the catalyst pyrolysis reactor effluent stream for the different configurations is shown in Table 3.

Figure 5:
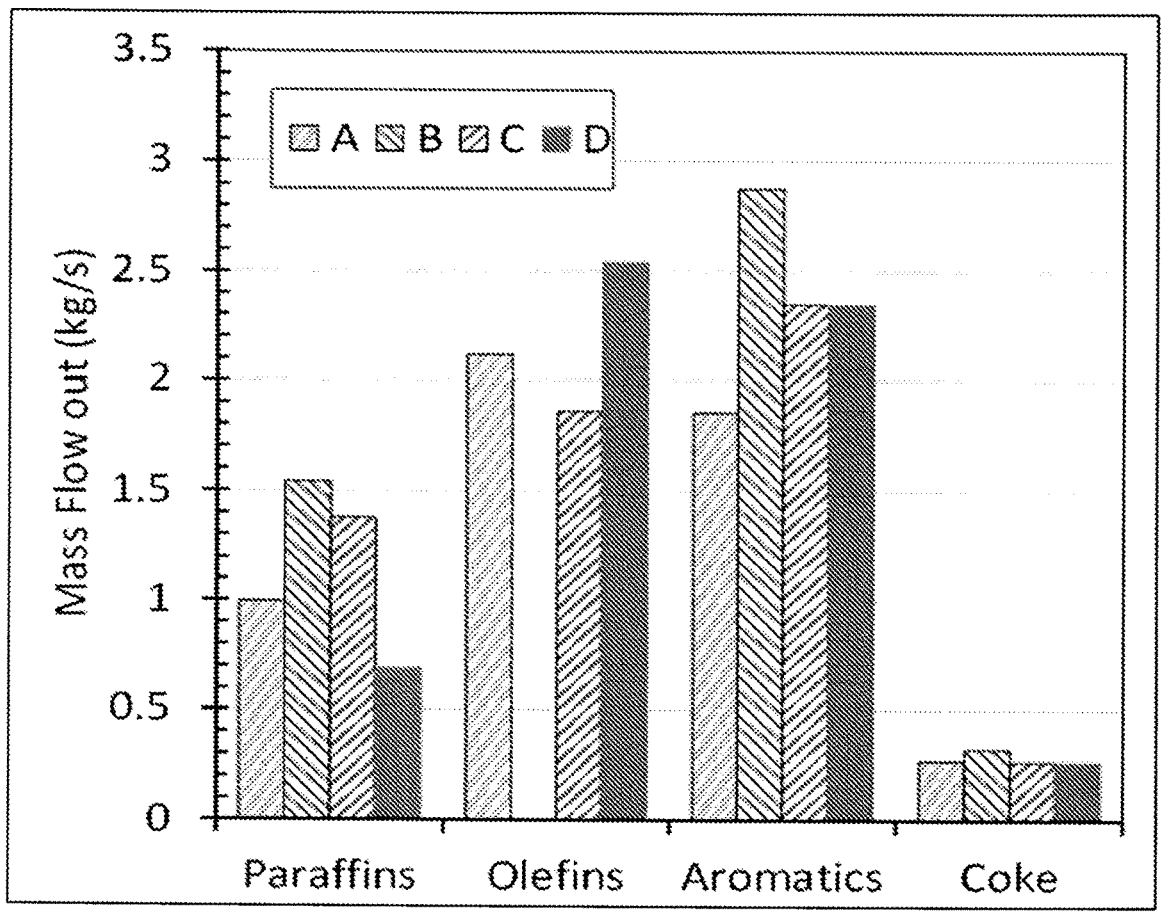
FIG. 5 shows product flowrates (kg/s) calculated for different PlasT-Cat configurations as shown in FIG. 4 for a 500 tpd plant.
Figure 6:
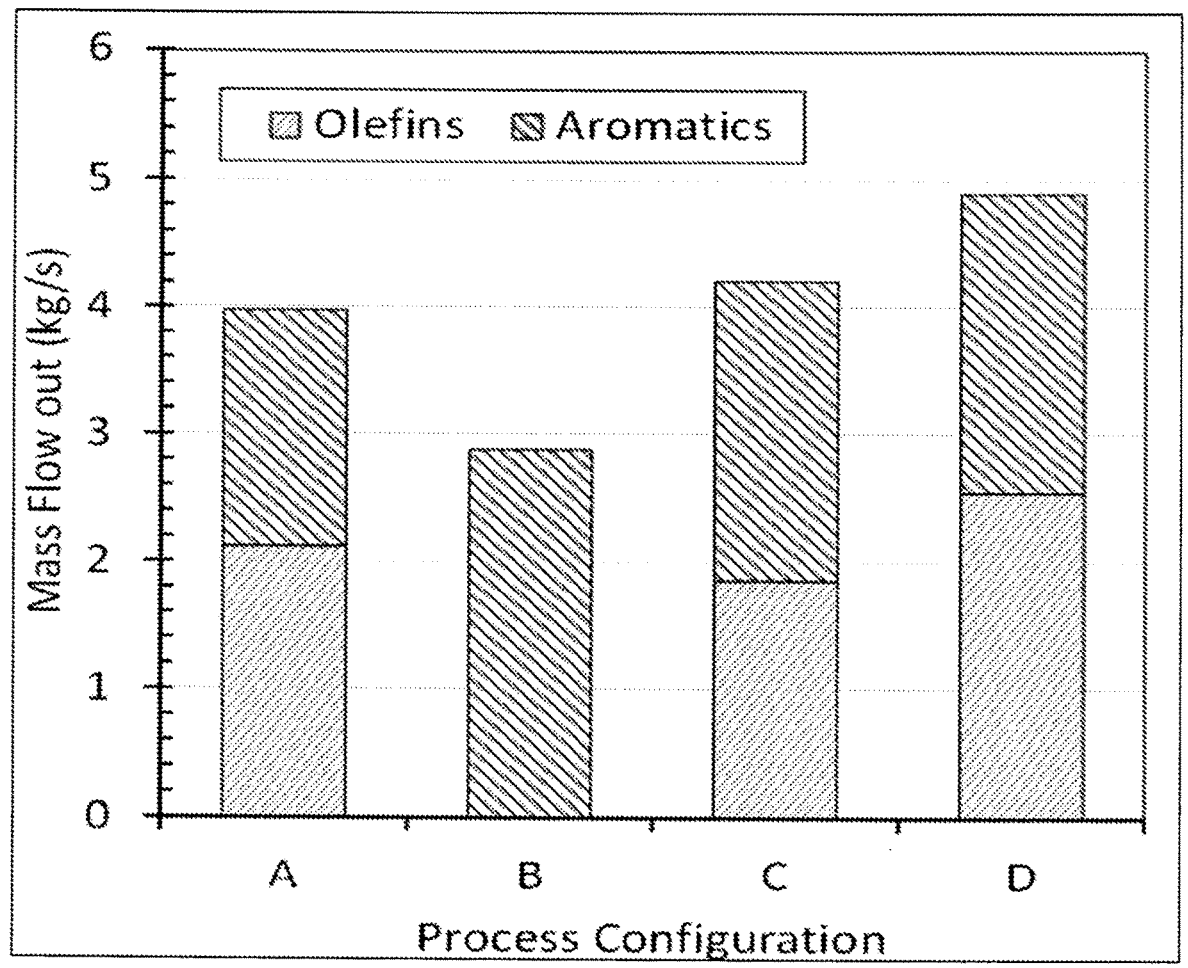
FIG. 6 shows a comparison of calculated olefins and aromatics yields (kg/s) from different PlasT-Cat configurations as shown in FIG. 4 for a 500 tpd plant.

The differential change in the yields of olefins and aromatics for cases (B) to (D) compared to the base case single pass case (A) is shown in Table 3. As can be seen, adding an alkane oxidation reactor into the recycle loop for the PlasT-cat conversion reactor will result in an overall net increase in the olefins+aromatics yield between 6 to 23%. This is further shown in Table 4 and FIG. 5, which show the product flowrates from the different configurations of the PlasT-Cat process at a 500 tpd capacity. As can be seen, configurations C and D, which include the alkane oxidation reactor will generate a higher rate of high value products (olefins and aromatics) compared to configurations A and B. This is also shown in FIG. 6, which only shows the total generated olefins+aromatics product from the different PlasT-Cat configurations and it is clear that configurations C and D, which include the alkane oxidation reactor, significantly outperform the direct recycle configuration (B).

The catalyst circulation rate between the PlasT-Cat reactor and the catalyst regenerator is determined by the heat balance between the two units. The circulating catalyst should provide sufficient heat to both maintain the PlasT-Cat reactor at reaction temperature, and provide the heat required for the melting and pyrolysis of the feed entering the reactor. The addition of an alkane oxidation reactor at 840° C., allows for a much higher temperature of the fluidization gas entering the PlasT-Cat reactor, when compared to the single pass configuration (A) or the olefins recycle configuration (B), in which the fluidization gas enters the reactor at 350° C., and in the case of configuration (B) this temperature could be lower to prevent excessive coking and thermal runaway in the recycle line. This will reduce the heat requirements for the PlasT-Cat reactor, and subsequently the required catalyst circulation rate. Using the conditions for the example, the catalyst circulation rate for cases (A) and (B) was calculated to be 158 kg/s, which is 21% higher than the catalyst circulation rate of 124 kg/s required for cases (C) and (D). A reduction in catalyst circulation requirement will also reduce the regenerator capital cost and improve plant economics.

TABLE 2

Summary of mass balance around the alkane oxidation reactor

| Species | Molar flow in (mol/s) | Mass Flow in (g/s) | Conversion | flow out Molar (mol/s) | Mol % | Mass flow out (g/s) | Mass % |
|---|---|---|---|---|---|---|---|
| $CH_4$ | 46.4 | 743.03 | 0.408 | 27.5 | 43% | 439.9 | 31.16% |
| $O_2$ | 20.9 | 668.73 | 0.983 | 0.4 | 1% | 11.4 | 0.81% |
| $C_{2+}$ Olefins | 0.0 | 0 | — | 2.2 | 4% | 78.7 | 5.58% |
| $C_{2+}$ Paraffins | 0 | 0 | — | 1.83 | 3% | 65.0 | 4.61% |
| $CO_x$ | 0.0 | 0 | — | 9.7 | 15% | 424.8 | 30.09% |
| $H_2O$ | 0.0 | 0 | — | 21.8 | 33% | 392.0 | 27.77% |

TABLE 3

Composition of the effluent stream leaving the catalytic pyrolysis reactor for all configurations

| Species | | (A) | (B) | (C) and (D) |
|---|---|---|---|---|
| Permanent Gas | wt % | 5.3% | 5.2% | 7.7% |
| Paraffins | wt % | 17.2% | 19.8% | 26.1% |
| Olefins | wt % | 36.6% | 29.4% | 21.6% |
| Aromatics | wt % | 32.0% | 37.1% | 29.7% |
| Water | wt % | 0.0% | 0.0% | 8.4% |
| Coke | wt % | 4.7% | 5.6% | 3.5% |
| Unknowns/Heavies | wt % | 4.3% | 3.0% | 3.1% |
| | | 100.0% | 100.0% | 100.0% |

TABLE 4

Flowrate from PlasT-Cat process boundary as shown in FIG. 4 (kg/s) for a 500 tpd plant

| | A | B | C | D |
|---|---|---|---|---|
| Product | Flowrate from PlasT-Cat process boundary as shown in FIG. 4 (kg/s) | | | |
| Paraffins | 0.996 | 1.541 | 1.375 | 0.687 |
| Olefins | 2.117 | 0 | 1.857 | 2.54 |
| Aromatics | 1.849 | 2.878 | 2.350 | 2.350 |
| Coke | 0.271 | 0.322 | 0.267 | 0.267 |

TABLE 5

Differential change in process yield for cases (B), (C), and (D) compared to case (A)

| Product | (B) | (C) | (D) |
|---|---|---|---|
| Olefins | −100% | −12% | 20% |
| Aromatics | 56% | 27% | 27% |
| Net increase in Olefins + Aromatics Yield | −27% | 6% | 23% |

What is claimed:

1. A method for producing olefins and aromatics comprising:
  a) feeding a stream comprising plastics to a catalytic pyrolysis reactor;
  b) reacting a stream comprising methane or ethane or alkanes having from 1 to 4 carbon atoms with oxygen in an oxidation reactor to produce a product stream comprising ethylene;
  c) passing at least a portion of the product stream from the alkane oxidation in b) to the catalytic pyrolysis reactor;
  d) reacting the combined plastics and alkane oxidation products stream in the catalytic pyrolysis reactor at a temperature above 350° C. to produce a vapor product, and;
  e) recovering olefins, or aromatics, or some combination thereof from the vapor product.

2. The process of claim 1 wherein the feed stream of plastics comprises waste plastics.

3. The process of claim 1 wherein the plastics feed stream comprises plastics chosen from among polyethylene (PE), polypropylene (PP), polystyrene (PS), polyesters, polyethylene terephthalate (PET), polyvinyl chloride (PVC), polyvinyl dichloride (PVDC), acrylonitrile-butadiene-styrene (ABS) copolymers, polyamide, polyurethane, polyethers, polycarbonates, poly(oxides), poly(sulfides), polyarylates, polyetherketones, polyetherimides, polysulfones, polyurethanes, polyvinyl alcohols, and polymers produced by polymerization of monomers, dienes, olefins, styrenes, acrylates, acrylonitrile, methacrylates, methacrylonitrile, diacids and diols, lactones, diacids and diamines, lactams, vinyl esters, or block copolymers thereof, or alloys thereof; thermoset polymers, epoxy resins; phenolic resins; melamine resins; alkyd resins; vinyl ester resins; unsaturated polyester resins; crosslinked polyurethanes; polyisocyanurates; crosslinked elastomers, including but not limited to, polyisoprene, polybutadiene, styrene-butadiene, styrene-isoprene, ethylene-propylene-diene monomer polymer; and mixtures thereof.

4. The process of claim 1 wherein the stream of plastics comprises plastics chosen from among polyethylene terephthalate (PET), high density polyethylene (HDPE), polyvinyl chloride (PVC) or polyvinylidene (PVCD), low density polyethylene (LDPE), polypropylene (PP), polystyrene (PS), or mixed resins, or some combination thereof.

5. The process of claim 1 wherein the feed mixture of plastics comprises copolymers such as: ethylene-propylene, EPDM, acrylonitrile-butadiene-styrene (ABS), nitrile rubber, natural and synthetic rubber, tires, styrene-butadiene, styrene-acrylonitrile, styrene-isoprene, styrene-maleic anhydride, ethylene-vinyl acetate, nylon 12/6/66, filled polymers, polymer composites, polymer composites comprising natural fibers, plastic alloys, other polymeric materials, and polymers or plastics dissolved in a solvent, or combinations thereof.

6. The process of claim 1 wherein the feed materials comprise materials obtained from polymer or plastic manufacturing processes as waste or discarded materials, post-consumer recycled polymer materials, materials separated from waste streams such as municipal solid waste (MSW), black liquor, wood waste, or other biologically produced materials, or combinations thereof.

7. The process of claim 1 wherein the residence time of the vapors in the catalytic pyrolysis reactor can be from 0.5 second to 480 seconds, or from 0.5 second to 240 seconds, or from 2 seconds to 60 seconds, or from 3 seconds to 30 seconds, or from 4 seconds to 15 seconds.

8. The process of claim 1 wherein the catalyst is a solid catalyst and the step of catalytically pyrolyzing comprises pyrolyzing in the presence of the solid catalyst in a fluidized bed reactor to produce a fluid product stream and used catalyst with coke.

9. The process of claim 1 wherein the catalyst comprises a zeolite.

10. The process of claim 1 wherein at least a portion of chlorine-containing plastics are selectively removed from the feed mixture.

11. The process of claim 1 wherein the plastic feed mixture is pretreated by pyrolyzing in a pyrolysis reactor by heating anaerobically to a temperature of between 25° and 300° C. to at least partially decompose the polymers.

12. The process of claim 11 wherein the plastic feed is heated to a temperature greater than 150° C. in a pyrolysis reactor, the vapors are removed, and the condensed phases are passed to the catalytic pyrolysis reactor or to a second pyrolysis reactor.

13. The process of claim 11 wherein solid co-reactant is chosen from among agricultural lime, calcium oxide, calcium hydroxide, magnesium oxide, magnesium hydroxide, limestone, or hydrotalcites, or some combination thereof.

14. The process of claim 11 wherein solid co-reactant material is separated from the products of a pretreatment pyrolysis and transferred to a combustion regenerator wherein carbonaceous materials are reacted with air and at least a portion of hot solid co-reactant material is returned to the pyrolysis reactor.

15. The process of claim 1 wherein the net movement of catalyst through a regenerator is in the upflow direction.

16. The process of claim 1 wherein the vapor products of the catalytic pyrolysis are passed to a separations and recovery facility.

17. The process of claim 1 wherein the mass yield of olefins in the product vapor mixture from the catalytic pyrolysis is at least 30%, or at least 40%, or at least 45%, or at least 50%, or at least 55%, or at least 60%, or from 20% to 90%, or from 30% to 70%, or from 45% to 60%, olefins based on the mass of the polymer feed.

18. The process of claim 1 wherein the mass yield of BTX in the gaseous product mixture from the catalytic reactor is at least 5%, at least 10%, or at least 20%, or at least 30%, or at least 35%, or at least 40%, or from 1% to 90%, for from 5% to 70%, from 10% to 60%, or from 20% to 50%, BTX based on the mass of the polymer feed.

19. The process of claim 16 wherein separations and recovery facility processes feed from a steam cracker or hydrocracker.

20. The process of claim 19 wherein carbon oxides or water or both are at least partially removed from the products of the catalytic pyrolysis products before the product mixture is fed to the separations portion of the steam cracker or hydrocracker.

21. The process of claim 19 wherein methane or ethane or C1-C4 alkanes separated in a separations portion of the steam cracker or hydrocracker are fed to the oxidation reactor.

22. The process of claim 19 wherein olefins or aromatics or both are recovered from a separations portion of the steam cracker or hydrocracker.

* * * * *